US011085022B2

(12) United States Patent
Zhang et al.

(10) Patent No.: US 11,085,022 B2
(45) Date of Patent: Aug. 10, 2021

(54) INFLAMMATION-TARGETED NEUTROPHIL GRANULOCYTE DRUG DELIVERY SYSTEM AND USE THEREOF

(71) Applicant: CHINA PHARMACEUTICAL UNIVERSITY, Jiangsu (CN)

(72) Inventors: Can Zhang, Nanjing (CN); Jingwei Xue, Nanjing (CN); Zekai Zhao, Nanjing (CN); Lei Zhang, Nanjing (CN); Yajing Wen, Nanjing (CN)

(73) Assignee: CHINA PHARMACEUTICAL UNIVERSITY, Nanjing (CN)

(*) Notice: Subject to any disclaimer, the term of this patent is extended or adjusted under 35 U.S.C. 154(b) by 21 days.

(21) Appl. No.: 15/512,726

(22) PCT Filed: Nov. 27, 2014

(86) PCT No.: PCT/CN2014/092340
§ 371 (c)(1),
(2) Date: Mar. 20, 2017

(87) PCT Pub. No.: WO2016/041250
PCT Pub. Date: Mar. 24, 2016

(65) Prior Publication Data
US 2017/0292113 A1 Oct. 12, 2017

(30) Foreign Application Priority Data
Sep. 20, 2014 (CN) .......................... 201410484577.4

(51) Int. Cl.
| | |
|---|---|
| *C12N 5/0787* | (2010.01) |
| *A61K 38/19* | (2006.01) |
| *A61K 38/22* | (2006.01) |
| *G01N 33/50* | (2006.01) |
| *A61K 31/337* | (2006.01) |
| *A61K 31/5383* | (2006.01) |
| *A61K 31/7105* | (2006.01) |
| *A61K 9/50* | (2006.01) |
| *A61K 9/127* | (2006.01) |
| *A61K 45/06* | (2006.01) |
| *A61K 31/192* | (2006.01) |
| *A61K 31/711* | (2006.01) |
| *C07K 14/715* | (2006.01) |
| *B82Y 5/00* | (2011.01) |

(52) U.S. Cl.
CPC .......... *C12N 5/0642* (2013.01); *A61K 9/1271* (2013.01); *A61K 9/5068* (2013.01); *A61K 31/192* (2013.01); *A61K 31/337* (2013.01); *A61K 31/5383* (2013.01); *A61K 31/711* (2013.01); *A61K 31/7105* (2013.01); *A61K 38/19* (2013.01); *A61K 38/22* (2013.01); *A61K 45/06* (2013.01); *C07K 14/715* (2013.01); *G01N 33/5047* (2013.01); *B82Y 5/00* (2013.01); *C07K 2317/00* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,441,168 B1 | 8/2002 | Muller et al. | |
| 2002/0090392 A1* | 7/2002 | Campbell | A61K 9/127 424/450 |
| 2004/0210289 A1* | 10/2004 | Wang | A61K 9/5094 607/116 |

FOREIGN PATENT DOCUMENTS

| | | |
|---|---|---|
| WO | 96/40060 A1 | 12/1996 |
| WO | 2011/046842 A1 | 4/2011 |

OTHER PUBLICATIONS

Batrakova et al. (Expert Opinion on Drug Delivery, 2011, pp. 415-433).*
Jain (International Journal of Pharmaceutics, 2003, p. 43-55).*
Ranneyand Huffaker, (Annals New York Academy of Sciences, 1987, p. 104-119).*
Afergan et al. (Journal of Controlled Release, 2008, p. 84-90).*
Hasenberg et al, (PLoS, 2011. p. 1-11).*
Sanyog Jain et al., "RGD-anchored magnetic liposomes for monocytes/neutrophils-mediated brain targeting," International Journal of Pharmaceutics, vol. 261, pp. 43-55, 2003.
Jing Qin et al., "Surface Modification of RGD-Liposomes for Selective Drug Delivery to Monocytes/Neutrophils in Brain," Chem. Pharm Bull., vol. 55, No. 8, 2007 pp. 1192-1197.
Qin, Jing et al., "Studies on RGD-Mediated Brain-Target Ferulic Acid Liposome," CDFD Medical Science and Technology Compiles, vol. 9, 2013.

(Continued)

Primary Examiner — Agnieszka Boesen
(74) Attorney, Agent, or Firm — Oliff PLC

(57) ABSTRACT

Disclosed are an inflammation-targeted neutrophil granulocyte drug delivery system and use thereof, wherein the drug delivery system includes neutrophil granulocytes and a therapeutic substance or a detectable substance loaded into the neutrophil granulocytes or onto the surface of the neutrophil granulocytes in a direct or indirect way. By using the neutrophil granulocytes as a carrier of a drug, the drug is actively targeted to an inflammatory site, thereby increasing the drug concentration at the inflammatory site. Under the stimulation of cytokines, the neutrophil granulocytes arriving at the inflammatory site are abnormally activated, disintegrate rapidly, and die in the way of "Neutrophil extracellular traps (NETs)". This helps to rapidly release the loaded drug to the targeted site, so as to improve the therapeutic effect and reduce the toxic and side effects.

17 Claims, 7 Drawing Sheets

(56) References Cited

OTHER PUBLICATIONS

Wang, Shuang et al., "Progress in Drug Delivery System for Brain Targeting," Chinese Journal of Pharmaceuticals, vol. 43, No. 2, 2012, pp. 137-142.
Jun. 12, 2015 International Search Report issued in International Patent Application No. PCT/CN2014/092340.
Jun. 12, 2015 Written Opinion Issued in International Patent Application No. PCT/CN2014/092340.

* cited by examiner

INFLAMMATION-TARGETED NEUTROPHIL GRANULOCYTE DRUG DELIVERY SYSTEM AND USE THEREOF

BACKGROUND

Technical Field

The present invention relates to the technical field of pharmaceutical preparations, and relates to an inflammation-targeted neutrophil granulocyte drug delivery system and use thereof, and particularly to a delivery system having neutrophil granulocyte as a carrier for targeting an inflammatory site.

Related Art

Inflammation refers to physiological responses elicited in tissues of an organism under the stimuli of traumas, bleeding, or infection with pathogens, including redness, heat, pain, and other symptoms. The inflammatory response is an important defense mechanism for removing harmful stimuli or pathogens and promoting the repair by the innate immune system, and includes infectious inflammation, nonspecific inflammation and allergic inflammation, depending on the causes of the disease. The infectious inflammation is caused by viruses, bacteria or bacterial products, and generally treated with antibiotics or antifungal agents. The non-specific inflammation is an inflammation or some stage of cellular tissue reaction caused in vivo or in vitro by a proinflammatory factor, such as ischemic-reperfusion injury and postoperative injury, and needs for systemic treatment. The allergic inflammation is an end manifestation of multiple hypersensitivity reactions, such as lupus dermatitis, and needs for anti-immune therapy.

At present, after the systemic administration to the inflammatory tissues, the targeting efficiency of the drug is low, and the systemic toxic effect is large, because of the unique pathological features of inflammation. The pathological features of inflammation mainly include local tissue alteration, exudation and proliferation. As the blood vessels at the inflammatory site are highly permeable, the protein-rich fluid and leukocytes are exuded therefrom, leading to elevated interstitial pressure in the inflammatory local tissues. Therefore, the high permeability of the blood vessels at the inflammatory site provides an opportunity for the drugs to come out from the blood vessel and reside in the inflammatory site. However, the elevated interstitial pressure in the inflammatory tissues precludes the drugs from entering the inflammatory site. Because of the low targeting of anti-inflammatory drugs, some infectious inflammations such as bacterial pneumonia, have not received treatment timely, resulting in drug resistance and leading to a high mortality. For the treatment of some inflammation-related diseases, such as ischemia-reperfusion brain injury and tumor recurrence after surgery, because the primary focus is peripherally surrounded by the non-specific inflammatory tissue, the targeting efficiency of the therapeutic agents is reduced, the efficacy is decreased, and the side effects are increased.

How to achieve the optimum diagnostic and therapeutic effect at the minimum dose is always a key problem obsessing the pharmacy practioners. With the development of nanotechnologies and increasing insights into the organisms, targeted delivery systems come into being accordingly. The targeted delivery systems mainly include passive, active, and physiochemical targeted delivery systems. Compared with the conventional delivery systems, although these emerging targeted delivery systems have achieved a qualitative leap, defects still exist, such as poor targeting, toxic side effects, and difficulty in achieving an expected diagnosis and therapeutic effect. Therefore, there is an urgent need for a highly efficient and low-toxic targeted delivery system.

The immune cells include mononuclear phagocytes (dendritic cells, monocytes and macrophages), neutrophil granulocytes and lymphocytes. Infiltration of immune cells during the inflammatory processes is the most important feature of inflammatory response, and as a "defender" for inflammation, the neutrophil granulocytes are attracted by chemokines to reach the inflammatory site at the first moment. At present, there is no report regarding use of the neutrophil granulocytes as a carrier in the delivery study of anti-inflammatory drugs, probes, and developing agents. Some scientific problems to be solved exist in loading of the drugs or nanopreparations into neutrophil granulocytes, for example, the way to load drugs, the amount of drugs, probes and developing agents loaded in the cells, the stability of the loaded drugs in the cell, and the maintenance of the intrinsic physiological activity of the cell carrier.

SUMMARY

To overcome the disadvantages existing in the prior art, the present invention provides a drug-loaded neutrophil granulocyte drug delivery system targeting an inflammatory tissue.

Another objective of the present invention is to provide use of the drug delivery system.

Another objective of the present invention is to provide a drug for treating inflammation.

An inflammation-targeted neutrophil granulocyte drug delivery system is provided, which comprises neutrophil granulocytes and a therapeutic substance or a detectable substance loaded into the neutrophil granulocytes or onto the surface of the neutrophil granulocytes in a direct or indirect way.

The therapeutic substance includes, but is not limited to, chemically synthesized drugs, natural medicines or natural drug extracts, and one or more of DNA, RNA, proteins or polypeptides having therapeutic effects. The detectable substance is one or more selected from probes and developing agents.

The indirect way means that a nanocarrier is used as a tool, the therapeutic substance or the detectable substance is loaded into the nanocarrier initially to prepare a nanopreparation, and then the nanopreparation is loaded into the neutrophil granulocytes or onto the surface of the neutrophil granulocytes.

The nanocarrier is preferably selected from a positively charged, a negatively charged, or a nearly neutral nanopreparation having a particle size of 1-1000 nm.

The nanocarrier includes, but is not limited to, gold nanoparticles/nanorods, magnetic nanoparticles, mesoporous silica nanoparticles, graphene, liposomes, nanoemulsions, nanospheres, nanocapsules, microspheres, pellets or dendritic polymers.

The drug is one or more selected from efferent nervous system drugs, central nervous system drugs, cardiovascular system drugs, hormones, respiratory and digestive system drugs, antibacterial or antiviral drugs, antineoplastic agents, and vitamins.

The drug is preferably one or more selected from the group consisting of antipyretic and analgesic agents, non-steroidal anti-inflammatory drugs, antineoplastic agents, antibiotics, diuretics, antihypertensive agents, blood lipid-lowering drugs, blood glucose-lowering agents, hormonal drugs or vitamins.

The drug is further preferably one or more of diazepam, phenytoin sodium, chlorpromazine, fluoxetine, methadone, meclofenoxate, bethanechol chloride, atrophic sulfate, isoprenaline, chlorpheniramine maleate, procaine hydrochloride, propranolol hydrochloride, verapamil hydrochloride, amiodarone hydrochloride, losartan, nitroglycerin, dobutamine, simvastatin, clopidogrel, prazosin, cimetidine, difenidol, cisaprid, bifendate, aspirin, indomethacin, mechlorethamine hydrochloride, fluorouracil, paclitaxel, amoxicillin, tetracycline, aminoglycoside, roxithromycin, chloramphenicol, levofloxacin, isoniazide, sulfadiazine, fluconazole, amantadine hydrochloride, fluoroquinol phosphate, glibenclamide, hydrochlorothiazide, prostaglandin, insulin, estradiol, vitamin A, or vitamin C.

Use of the inflammation-targeted neutrophil granulocyte drug delivery system according to the present invention in the preparation of drugs or agents for treating or diagnosing inflammation and/or inflammation related diseases is provided.

The inflammation includes infectious inflammation, nonspecific inflammation, allergic inflammation, and inflammation-related diseases.

The infectious inflammation includes inflammations caused by viruses, bacteria or bacterial products. The nonspecific inflammation includes physical inflammations, including redness or pain caused by surgery or trauma. The allergic inflammation includes lupus dermatitis, allergies asthma, and rheumatoid arthritis. The inflammation-related diseases include treatment of postoperative recurrence of tumors, atherosclerosis, and hypoxic ischemic encephalopathy.

In the present invention, the therapeutic substance or the detectable substance is initially encapsulated in a differently charged nanocarrier (positively charged, negative charged, and nearly neutral, particle size 1-1000 nm), and then the drug-loaded nanocarrier (that is, nanopreparation) is loaded into the neutrophil granulocytes or onto the surface of the neutrophil granulocytes; or the therapeutic substance or the detectable substance is directly loaded into the neutrophil granulocytes or onto the surface of the neutrophil granulocytes, thereby successfully preparing a delivery system having neutrophil granulocytes as a carrier. The prepared neutrophil granulocyte drug delivery system is injected intravenously into human, which is stimulated by the released chemotactic factors from the inflammatory region during the blood circulation, travels across the blood vessel in the inflammatory site, and actively localizes in the inflammatory site along the concentration gradient of the chemotactic factors, thus increasing the drug concentration at the inflammatory site and ensuring the therapeutic efficacy. Studies show that the infectious inflammation, nonspecific inflammation, allergic inflammation and inflammation-related diseases such as acute inflammation caused by tumor surgery are all associated with the recruitment of neutrophil granulocytes. Therefore, by using the neutrophil granulocytes as a drug delivery system for treating inflammation or inflammation-related diseases, for example, the treatment of relapsed tumor after tumor surgery by means of acute inflammation, the drug accumulation in the target site is effectively increased, the efficacy of the drug is improved, and the toxic side effect is reduced. In summary, the therapeutic substance or the detectable substance can be successfully delivered to the site of inflammation-related diseases by the neutrophil granulocytes loaded with the therapeutic substance or the detectable substance with the induction of inflammatory factors, and acts to treat or diagnose the disease and inhibits the occurrence and development of the disease.

A medicament for the treatment of inflammation and/or inflammation related diseases comprises the inflammation-targeted neutrophil granulocyte drug delivery system of the present invention.

The therapeutic substance in the neutrophil granulocyte drug delivery system may be a medicament having a therapeutic effect on inflammation and/or inflammation-related diseases in a conventional route of administration, and includes, but is not limited to, nervous system drugs; cardiovascular and cerebrovascular drugs; blood, respiratory and digestive system drugs; endocrine system and immunoregulatory drugs, for example, immune enhancers such as interferon, and immunosuppressive agents such as cyclosporine.

An agent for diagnosing inflammation and/or inflammation-related diseases comprises the inflammation-targeted neutrophil granulocyte drug delivery system according to the present invention.

The diagnostic material in the neutrophil granulocyte drug delivery system includes, but is not limited to, probes such as DNA probes and fluorescent probes, and contrast agents such as iodine preparations commonly used for X-ray observation, barium sulfate and magnetic resonance imaging contrast agents such as gadopentetate dimeglumine and so on Some of the concepts involved in the present invention are defined as follows.

Nanocarrier: namely nanoscale drug carrier, which is a sub-microparticulate drug carrier delivery system of nanoscale microscopic category. By encapsulating drugs in the sub-microparticles (i.e., the nanocarrier), the rate of drug release can be adjusted, the permeability through a biological membrane is increased, the in-vivo distribution is changed, and the bioavailability is enhanced.

The nanopreparation of the present invention can be prepared according to any of the methods reported in the prior art Preparation of Liposomes:

(1) Preparation of Liposome in which the Drug is Dispersed in an Organic Phase

Liposome that is suitable for the preparation of lipophilic drugs. Specifically, such methods include thin film dispersion, injection, proliposome preparation method, ultrasonic dispersion and the like.

(2) Preparation of Liposome in which the Drug is Dispersed in an Aqueous Phase

Liposome that is suitable for the preparation of water-soluble drugs, where the drugs are required to have good stability. In particular, such methods include reverse-phase evaporation, double-emulsion method, melting, freezing and thawing, freeze drying, treatment with surfactants, calcium-mediated fusion method, centrifugation and other methods.

Inflammation: the defensive response of living tissues having vascular system to damage factors.

Beneficial Effects

Neutrophil granulocytes are the most abundant type of white blood cells, which account for 50% to 70% of the white blood cells, are readily available from the patient, and provide abundant reserves for drug delivery.

In the present invention, neutrophil granulocytes are used as a drug delivery carrier. The neutrophil granulocytes protect the loaded drugs, probes or developing agents from clearance by the reticuloendothelial system, thereby prolonging the half-life, effectively controlling the release, and reducing the immunogenicity and the toxic side effect. Moreover, as a carrier, the neutrophil granulocytes can travel across a hydrophobic barrier to arrive the locus of disease successfully, thus increasing the drug concentration at the target site. Further, the neutrophil granulocytes are chemotactic, and can target and release drugs to injury, inflammatory, and tumor site. Therefore, the neutrophil granulocytes serve as a low-toxic transporter capable of targeted drug delivery, prolonging the circulation time, and reducing the toxicity to cells and tissues.

Therefore, in view of the advantages of neutrophil granulocytes as a drug delivery system, when the neutrophil granulocytes are used as a carrier of a drug, the drug can be actively targeted to the inflammatory site, thus increasing the drug concentration at the target site. Under the stimulation of cytokines, the neutrophil granulocytes arriving at the inflammatory site are abnormally activated, disintegrate rapidly, and die in the way of "Neutrophil extracellular traps (NETs)". This helps to rapidly release the loaded drug to the targeted site, so as to improve the therapeutic effect and reduce the toxic and side effects.

Compared with the prior art, the invention has the following advantages:

1. The neutrophil granulocyte drug delivery system successfully prepared in the present invention can reach the inflammatory tissue along the concentration gradient of the chemotactic factors, thereby successfully solving the problem of poor targeting of the drugs, probes or developing agents.

2. The neutrophil granulocyte drug delivery system prepared in the present invention ensures a high drug load on/in the neutrophil granulocytes via the mediation of the nanocarrier and avoids the influence of the drugs on the physiological activity of the neutrophil granulocyte.

3. The neutrophil granulocyte drug delivery system prepared in the present invention has a high drug load on/in the cells, because the neutrophil granulocytes are natural immune cells having potent phagocytosis in the organisms.

4. The drug carrier neutrophil granulocyte used in the present invention is the most abundant type of white blood cells in human, which is readily available from the patient, and disintegrates in a unique manner of death after being abnormally activated at the inflammatory site, thereby rapidly and thoroughly releasing the loaded drug to the inflammatory tissue. Thus, the present invention is of great development and application value in clinic.

DETAILED DESCRIPTION

The technical solutions of the present invention are further described with reference to examples. However, the examples are merely illustrative of the technical solutions and effects of the present invention, instead of limiting the protection scope of the present invention.

Example 1

Targeting and Pharmacodynamic Evaluation of Differently Charged Paclitaxel-Liposome-Neutrophil Granulocyte Drug Delivery Systems in Postoperative Glioblastoma Model Mice I. Separation and Purification of Bone Marrow Neutrophil Granulocytes 100% Percoll was prepared with stock Percoll:10× PBS 9:1 (v/v), and then diluted with 1× PBS, to prepare a 55%, 65%, and 68% (v/v) Percoll separation medium. Two layers of the separation media from large to small in density were slowly and uniformly superimposed to prepare a 55%-65% two-layer Percoll separation medium. The freshly extracted mouse tibial bone marrow cells were diluted with 1× PBS, to prepare a single cell suspension. The suspension was slowly and uniformly 1:1 (v/v) added to the top of the 55%-65% Percoll separation medium prepared above, and centrifuged at 1000 g for 30 min. The bone marrow cells in the interphase of the 55%-65% separation medium were extracted, washed and resuspended in one volume of 1× PBS, and then slowly superimposed onto the 68% Percoll separation medium, and centrifuged at 1000 g for 30 min. The bone marrow cells in the 68% separation medium layer were extracted, washed twice with one volume of 1× PBS, and resuspended in RPMI 1640 medium to prepare a mouse bone marrow neutrophil granulocyte suspension for later use.

Figure 1:
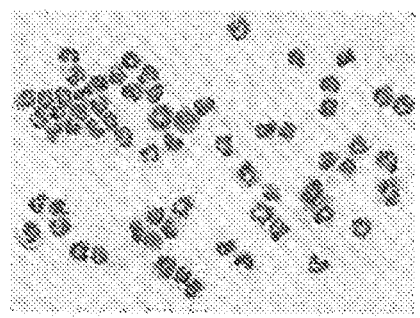
FIG. 1 shows morphological identification of 65%/68% Percoll separation layer by Wright-Giemsa Stain.

The extracted cells were stained with red fluorescently labeled cell surface protein Gr-1 antibody (Beijing Dakewei Biotechnology Co., Ltd.), incubated for 30 min at 31° C. in 5% $CO_2$, and detected for the purity by flow cytometry. The viability of the extracted cells was determined to be about 98% by trypan blue. The morphological purity of the extracted cells was determined by using a Wright-Giemsa Stain Solution. The result is shown in FIG. 1. Most of the isolated neutrophil granulocytes have a mature rod-shaped or lobulated nucleus. After staining the extracted cells with red fluorescently labeled cell surface protein Gr-1 antibody, the result shows that the purity of the extracted neutrophil granulocyte is higher than 90%.

II. Preparation of Paclitaxel-Liposome-Neutrophil Granulocyte Drug Delivery Systems (PTX-Liposome-NEs)

1. Preparation of Differently Charged Paclitaxel-Liposomes

Three differently charged liposomes-paclitaxel were prepared by thin film dispersion. The preparation steps were specifically as follows.

Prescribed amounts of the substances below were accurately weighed.

1) Positively charged liposome: soybean lecithin 90 mg+cationic liposome 10 mg+cholesterol 10 mg+paclitaxel 5 mg;
2) Nearly neutral liposome: neutral liposome 100 mg+cholesterol 10 mg+paclitaxel 5 mg;
3) Negatively charged liposome: soybean lecithin 100 mg+cholesterol 10 mg+paclitaxel 5 mg;

Prescribed amounts of the substances were dissolved in a mixed solvent of chloroform/methanol (2:1, v:v), and mixed until uniform. The mixture was spin dried under vacuum in a water bath at 40° C. to form a film, which was placed in a vacuum desiccator overnight to completely remove the organic solvent. Then, the lipid film was hydrated with ultra-pure water at 37° C. and the resulting lipid suspension was dispersed in an ice bath by an ultrasonic cell disruptor, and filtered through a 0.45 μm and 0.22 μm microporous membrane respectively, to obtain three differently charged PTX-liposomes.

The drug load and encapsulation rate of the PTX-liposome were determined by HPLC, the particle size was measured by a laser particle size analyzer, and the potential was determined. The result is shown in Table 1.

TABLE 1

| Preparation | Potential (mV) | Particle size (nm) | Drug load (%) | Encapsulation rate (%) |
|---|---|---|---|---|
| Positively charged liposome | 30.67 ± 2.83 | 100.9 ± 0.5 | 3 | 75 |
| Nearly neutral liposome | −5.42 ± 0.74 | 110.2 ± 2.3 | 3.5 | 85 |
| Negatively charged liposome | −20.48 ± 1.15 | 104.3 ± 0.9 | 4 | 90 |

Figure 2:
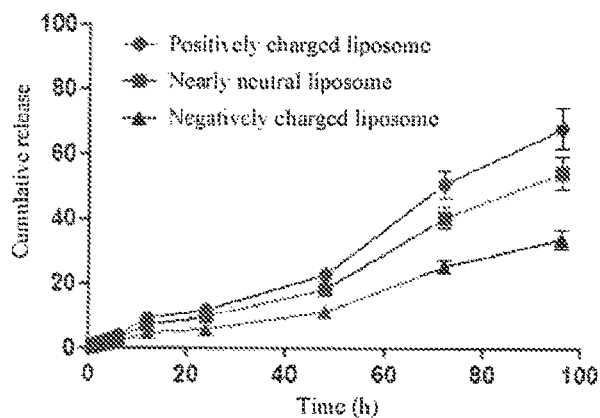
FIG. 2 shows release of differently charged PTX-liposomes.

The in-vitro release was determined by dialysis. The result is shown in FIG. 2. The result shows that the PTX-liposomes release the drug slowly in the duration of the assay, and the cumulatively released amount is less than 20% in 24 hrs. Therefore, the PTX-liposomes have a slow release property.

2. Preparation of Paclitaxel-Liposome-Neutrophil Granulocyte Drug Delivery Systems (PTX-Liposome-NEs)

500 μL of a freshly prepared neutrophil granulocyte suspension was inoculated into a 24-well plate at a density of 1×10⁶ cells/well, and stably incubated for 1 hr with a serum-free RPIM 1640 medium at 37° C. in 5% $CO_2$. The medium was removed. The three differently charged PTX-liposomes were diluted with a serum-free RPIM 1640 medium to a concentration of 100 μg PTX/ml. The diluted solution was added to the 24-well plate, and incubated for 50 min at 37° C. The medium containing the preparation was discarded. The remainder was washed three times with PBS at 4° C., to obtain differently charged paclitaxel-liposome-neutrophil granulocyte drug delivery systems.

Figure 3:
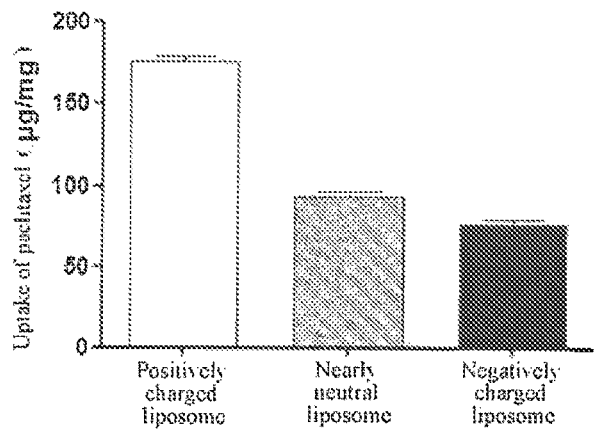
FIG. 3 shows uptake of differently charged liposomes by neutrophil granulocytes.

The uptake of differently charged liposomes by neutrophil granulocytes was determined by HPLC. The result is shown in FIG. 3. The result shows that the uptake of positively charged liposome by the neutrophil granulocyte is significantly higher than that of the nearly neutral and negatively charged liposomes, which provides a guarantee for the preparation of a drug delivery system with high drug load.

Figure 4:
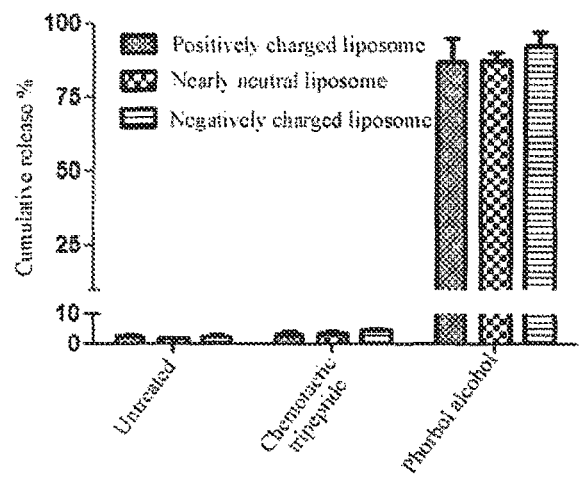
FIG. 4 shows residence of three differently charged PTX-liposomes in neutrophil granulocytes under various physiological and pathological conditions simulated in vitro.

Three physiological and pathological environments including the normal physiological conditions, the process of chemotaxis, and the inflammatory site were simulated in vitro with RPMI 1640 medium 7.4, 10 nM chemotactic tripeptide and 100 nM phorbol alcohol respectively. The residence of the three differently charged PTX-liposomes in neutrophil granulocytes at 4 hrs under various physiological and pathological conditions was measured by HPLC. The result is shown in FIG. 4. The result shows that the cumulative release of the drug from the cell drug delivery system is only 5% of the total uptake during the process of chemotaxis, and the release is slow. Where the neutrophil granulocytes arrive at the target site and are abnormally activated, the cumulative release of the drug accounts for 85% of the total uptake, thereby ensuring that most of the drug can be delivered to the target site and exert a curative effect.

III. Establishment of Postoperative Glioblastoma Mice Model

KM mice were anesthetized by intraperitoneal injection of chloral hydrate and immobilized in a stereotactic head frame. Murine glioblastoma cells G422 were injected into the right caudate nucleus of the mice by a microinjector (by surgically exposing the landmark of skull, drilling a hole of 1.2 mm at 4 mm to the right of and 1 mm before the anterior fontanelle, and inserting the needle to subdural 5 mm). The mice were sutured, and put back into the cage after disinfection.

IV. Relative Ratio and Brain Targeting Efficiency of Paclitaxel-Liposome-Neutrophil Granulocyte Drug Delivery Systems (PTX-Liposome-NEs) In Postoperative Glioblastoma Model Mice 1. Dosing Regimen 144 postoperative glioblastoma model mice were randomized to 4 groups, each group having 36 animals. Before administration, the mice were fasted, but allowed to free access to water overnight. The 4 groups of tumor-bearing mice were intravenously injected with the commercially available paclitaxel preparation Taxol and the differently charged paclitaxel-liposome-neutrophil granulocyte drug delivery systems at the tail respectively, where the dosage of PTX was 5 mg/kg in each case. 0.167 h, 0.5 h, 1 h, 2 h, 4 h, 8 h, 12 h, 24 h, 48 h, 72 h, 96 h, and 120 h after administration, the eyeballs were removed from 3 tumor-bearing mice in each group to collect the blood, and then the mice were sacrificed. The heart, liver, spleen, kidney, and brain tissues were removed, washed with physiological saline, and weighed after the residual physiological saline was aspirated off with filter paper. The tissues were treated as follows, and the PTX concentration contained in the tissue samples at each time point was determined by HPLC.

2. Sample Treatment

The tissue samples (heart, liver, spleen, lung, kidney, and brain) from the tumor-bearing mice were weighed, placed in a blood collection tube, added with 2 mL physiological saline, and dispersed by a tissue homogenizer at a high speed, to give a tissue homogenate. 200 μL acetonitrile was added to 200 μL of each tissue homogenate, vortexed for 5 min, and centrifuged for 10 min at 10000×g. The supernatant was analyzed by HPLC and the content of PTX in the tissue samples was calculated according to a linear equation.

3. HPLC Method

Chromatographic column: Inertsil®ODS-SP column (250 mm×4.6 mm×5 μm, GL Sciences Inc., Japan)
Mobile phase: methanol:water=80:20 (v:v)
Detection wavelength: 227 nm
Column temperature: 35° C.
Flow rate: 1.0 mL/min
Volume of injection: 20 μL The tissue homogenate does not interfere with the separation and determination of PTX, and the retention time of PTX is about 8.1 min.

5. In-Vivo Distribution in Mice

TABLE 2

Distribution of Taxol in various organs

| Organ Time (h) | Heart (μg/g) | Liver (μg/g) | Spleen (μg/g) | Kidney (μg/g) | Brain (μg/g) |
|---|---|---|---|---|---|
| 0.5 | 8.26 | 3.71 | 8.85 | 5.62 | 0.37 |
| 1 | 7.69 | 2.08 | 7.23 | 4.85 | 0.11 |
| 2 | 7.37 | 1.95 | 6.33 | 3.36 | — |
| 4 | 6.45 | 1.04 | 5.81 | 2.65 | — |
| 8 | 5.57 | 0.85 | 4.37 | 2.08 | — |
| 12 | 3.11 | — | 2.64 | — | — |

TABLE 3

Distribution of positively charged nanopreparation-neutrophil granulocyte drug delivery system in various organs

| Organ Time (h) | Heart (μg/g) | Liver (μg/g) | Spleen (μg/g) | Kidney (μg/g) | Brain (μg/g) |
|---|---|---|---|---|---|
| 12 | — | 3.16 | 7.15 | 0.61 | 8.83 |
| 24 | — | 2.41 | 6.84 | 0.45 | 7.25 |
| 48 | — | 1.52 | 5.01 | 0.32 | 6.81 |
| 72 | — | 0.97 | 3.4 | 0.17 | 5.74 |
| 96 | — | 0.55 | 1.26 | — | 3.28 |
| 120 | — | 0.21 | 0.75 | — | 1.23 |

TABLE 4

Distribution of nearly neutral nanopreparation-neutrophil granulocyte drug delivery system In various organs

| Organ Time (h) | Heart (μg/g) | Liver (μg/g) | Spleen (μg/g) | Kidney (μg/g) | Brain (μg/g) |
|---|---|---|---|---|---|
| 12 | — | 3.00 | 6.79 | 0.58 | 8.39 |
| 24 | — | 2.29 | 6.50 | 0.43 | 6.89 |
| 48 | — | 1.44 | 4.76 | 0.30 | 6.47 |
| 72 | — | 0.92 | 3.23 | 0.16 | 5.45 |
| 96 | — | 0.52 | 1.20 | — | 3.12 |
| 120 | — | 0.20 | 0.71 | — | 1.17 |

TABLE 5

Distribution of negatively charged nanopreparation-neutrophil granulocyte drug delivery system in various organs

| Organ Time (h) | Heart (μg/g) | Liver (μg/g) | Spleen (μg/g) | Kidney (μg/g) | Brain (μg/g) |
|---|---|---|---|---|---|
| 12 | — | 2.78 | 6.29 | 0.54 | 7.77 |
| 24 | — | 2.12 | 6.02 | 0.40 | 6.38 |
| 48 | — | 1.34 | 4.41 | 0.28 | 5.99 |
| 72 | — | 0.85 | 2.99 | 0.15 | 5.05 |
| 96 | — | 0.48 | 1.11 | — | 2.89 |
| 120 | — | 0.18 | 0.66 | — | 1.08 |

The results of HPLC analysis show that the commercially available paclitaxel preparation Taxol has the largest distribution in the liver, followed by the distribution in the heart, spleen and kidney, with the distribution in the brain being extremely small. Compared with Taxol, in the group with neutrophil granulocyte drug delivery system, the paclitaxel has the largest distribution in the brain and spleen, followed by the distribution in the liver and kidney, with the distribution in other organs being less. There is no significant difference in the distribution of differently charged nanopreparation-neutrophil granulocyte drug delivery systems in various organs.

5. Targeting Evaluation $AUC_{0-\infty}$, $AUC_{0-120\,h}$ and other parameters in the tissues after Taxol and the differently charged PTX-liposome-neutrophil granulocyte drug delivery systems are intravenously injected are calculated by a statistical method in Kinetic 4.0 pharmacokinetic program, and then the relative ratio (Re) and the brain targeting efficiency (Te) are calculated.

The relative ratio (Re) refers to the ratio of AUCs of the differently charged PTX-liposome-neutrophil granulocyte drug delivery systems and Taxol in the brain. A larger Re indicates that the preparation is more potent in targeting the brain tissue than Taxol. The brain targeting efficiency (Te) refers to the ratio of AUCs of the same preparation in the brain and in other tissues. Where Te is greater than 1, it is indicated that the selectivity of the preparation for the brain is larger than that for other comparative tissues. The larger the Te is, the higher the selectivity of the preparation for the brain will be, as compared with the selectivity for other comparative tissues.

Figure 5:
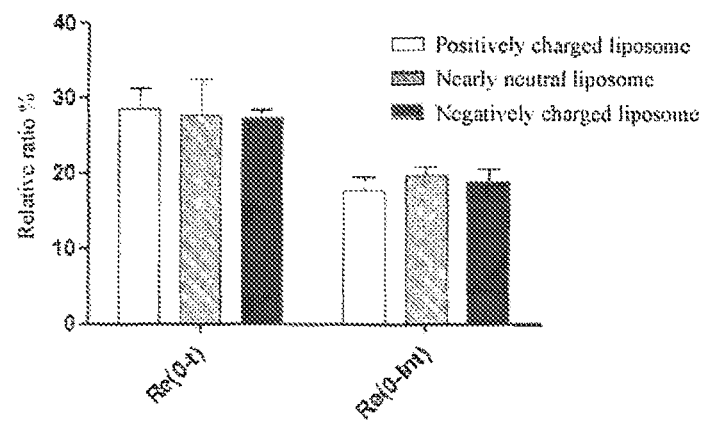
FIG. 5 shows relative ratios (Re) of negatively charged, nearly neutral, and positively charged nanopreparation-neutrophil granulocyte drug delivery systems relative to a commercially available preparation in the inflammatory site of postoperative glioblastoma model mice after administration.
Figure 6:
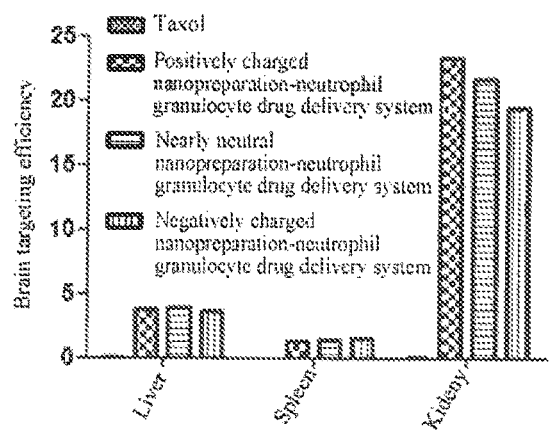
FIG. 6 shows brain targeting efficiencies (Te) of a commercially available preparation and negatively charged, nearly neutral, and positively charged nanopreparation-neutrophil granulocyte drug delivery systems in mice after administration.

The $Re_{(O-t)}$ and $Re_{(O-Inf)}$ in brain of the differently charged PTX-liposome-neutrophil granulocyte drug delivery systems relative to Taxol are shown in FIG. 5, and the Te is greater than 1 in each case (FIG. 6), suggesting that the neutrophil granulocyte drug delivery system is excellent in targeting the brain, and can penetrate the brain-blood-barrier (BBB) rapidly, and deliver the drug efficiently to the brain tissue.

Figure 7:
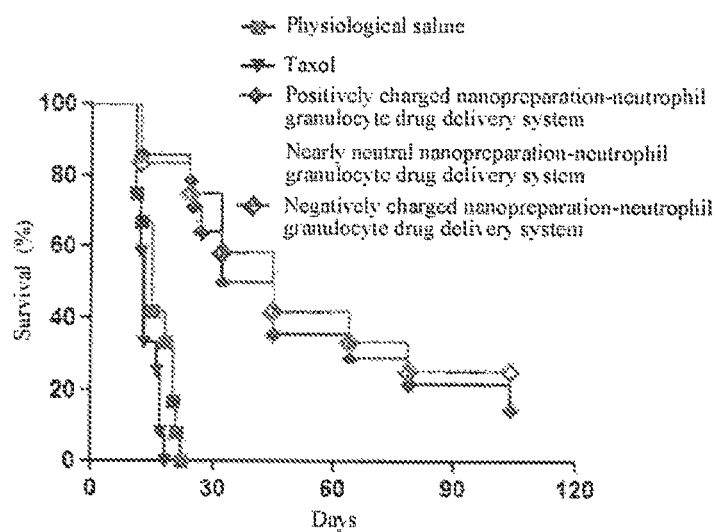
FIG. 7 shows survival time curves of postoperative glioblastoma model mice administered with physiological saline, blank neutrophil granulocytes, a commercially available preparation Taxol, and negatively charged, nearly neutral, and positively charged nanopreparation-neutrophil granulocyte drug delivery systems.

V. Pharmacodynamic Evaluation of Drug-Loaded Neutrophil Granulocyte Drug Delivery Systems in Postoperative Glioblastoma Model Mice 60 postoperative glioblastoma model mice were randomized to 5 groups, each group having 12 animals. The 5 groups included a postoperative physiological saline group, a group with commercially available preparation Taxol, and groups with differently charged paclitaxel-liposome-neutrophil granulocyte drug delivery systems. The dosage in the Taxol group was 5 mg PTX/kg; and the animals in the groups with differently charged paclitaxel-liposome-neutrophil granulocyte drug delivery systems were each intravenously injected with about $5 \times 10^6$ NEs/animal, and the dosage was about 5 mg PTX/kg. All the animals were administered at days 1, 2, 3, 4, 6, 8, and 10 after surgery, and a total of 7 administrations were presented. The day when the mice were primarily inoculated with murine glioblastoma cells G422 was recorded as day 0. The survival time of the mice in each group was recorded, and a survival time curve was plotted. The result is shown in FIG. 7. It can be seen from FIG. 7 that the survival time of the postoperative glioblastoma model mice in the groups with differently charged paclitaxel-liposome-neutrophil granulocyte drug delivery systems can be considerably extended. This confirms that the neutrophil granulocyte drug delivery systems prepared in the present invention can effectively inhibit the occurrence and development of inflammation-related diseases.

Example 2

Targeting and Pharmacodynamic Evaluation of Levofloxacin-Cationic Liposome-Neutrophil Granulocyte Drug Delivery System in Streptococcal Pneumonia Model Mice I. Preparation and Characterization of Levofloxacin-Loaded Neutrophil Granulocyte Drug Delivery System The extraction and purification of neutrophil granulocytes were the same as those in Example 1. 10 mg levofloxacin was used to prepare a levofloxacin-cationic liposome, and the preparation process was the same as that in Example 1.

The drug load and encapsulation rate were determined by HPLC, the particle size was measured by a laser particle size analyzer, and the potential was determined. The result is shown in Table 6.

TABLE 6

| Preparation | Potential (mV) | Particle size (nm) | Drug load (%) | Encapsulation rate (%) |
| --- | --- | --- | --- | --- |
| Levofloxacin-cationic liposome | 25.23 ± 0.57 | 112.5 ± 0.7 | 3.2 | 92 |

Figure 8:
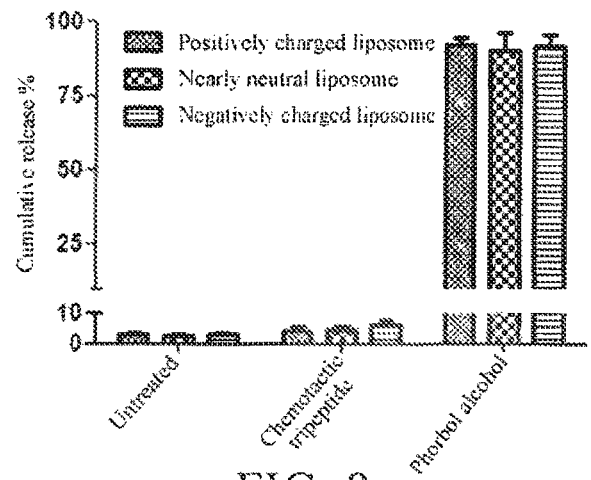
FIG. 8 shows residence of three differently charged levofloxacin-liposomes in neutrophil granulocytes under various physiological conditions simulated in vitro.

The residence of three differently charged levofloxacin-liposomes in neutrophil granulocytes under various physiological conditions simulated in vitro was measured by HPLC. The result is shown in FIG. 8. It can be seen from FIG. 8 that during the simulated normal blood circulation and the process of chemotaxis of inflammatory factors, the release of the drug is only 7% of the total uptake; and in the inflammatory site, the release of the drug is up to 90% of the total uptake when the neutrophil granulocyte are abnormally activated, confirming that the drug can be rapidly and thoroughly released from the cells at the inflammatory site.

II. Establishment of Inflammation Animal Model

Streptococcal pneumonia mouse model: Clean-grade male mice weighed 18-22 g were anesthetized by intraperitoneal injection of 10% chloral hydrate at a dosage of 0.3 ml/100 g (300 mg/kg), and 40 μL of the prepared $10^6$ CFU/mL Streptococcus pneumoniae suspension was dripped via the nasal cavity.

III. Targeting Study of Neutrophil Granulocyte Drug Delivery System in Inflammation Model Mouse 1. Dosing Regimen 72 mice with inflammation were randomized to 2 groups, each group having 36 animals. Before administration, the mice were fasted, but allowed to free access to water overnight. The 2 groups of mice with inflammation were intravenously injected with the commercially available levofloxacin and the levofloxacin-cationic liposome-neutrophil granulocyte drug delivery system at the tail respectively, where the dosage of levofloxacin was 10 mg/kg in each case, the mice were sacrificed 0.167 h, 0.5 h, 1 h, 2 h, 4 h, 8 h, 12 h, 24 h, 48 h, 72 h, 96 h, and 120 h after administration. The heart, liver, spleen, kidney, and lung tissues were removed, washed with physiological saline, and weighed after the residual physiological saline was aspirated off with filter paper. The tissues were treated as follows, and the levofloxacin concentration contained in the tissue samples at each time point was determined by HPLC.

2. Sample Treatment

The tissue samples (heart, liver, spleen, kidney, and lung) from the mice with inflammation were weighed, placed in a blood collection tube, added with 2 mL physiological saline, and dispersed by a tissue homogenizer at a high speed, to give a tissue homogenate. 200 μL acetonitrile was added to 200 μL of each tissue homogenate, vortexed for 5 min, and centrifuged for 10 min at 10000×g. The supernatant was analyzed by HPLC and the content of levofloxacin in the tissue samples was calculated according to a linear equation.

3. HPLC Method

Chromatographic column: Inertsil®ODS-SP column (250 mm×4.6 mm×5 μm, GL Sciences Inc., Japan)

Mobile phase: methanol:water=80:20(v:v), adjusted to pH 3.5 with 0.01 mol/L monopotassium phosphate (pH 3.0):acetonitrile=45:55 (v:v) and methanol:acetonitrile:(0.0 mol/L) monopotassium phosphate:(0.5 mol/L) tetrabutyl ammonium bromide=(10:10:80:4)

Detection wavelength: 294 nm
Column temperature: room temperature
Flow rate: 1.0 mL/min
Volume of injection: 20 μL The tissue homogenate does not interfere with the separation and determination of levofloxacin, and the retention time of levafloxacin is about 5.6 min.

6. In-Vivo Distribution in Mice

TABLE 7

Distribution of levofloxacin in various organs

| Organ Time (h) | Heart (μg/g) | Liver (μg/g) | Spleen (μg/g) | Kidney (μg/g) | Lung (μg/g) |
|---|---|---|---|---|---|
| 0.5 | 8.35 | 11.41 | 6.05 | 1.58 | 0.46 |
| 1 | 4.70 | 9.22 | 3.85 | 3.32 | 0.23 |
| 2 | 2.16 | 7.58 | 1.92 | 2.40 | 0.15 |
| 4 | 1.32 | 6.50 | 0.99 | 1.99 | — |
| 8 | 0.90 | 4.79 | 0.20 | 0.55 | — |
| 12 | 0.59 | 1.69 | — | 0.24 | — |

TABLE 8

Distribution of levofloxacin-cationic liposome-neutrophil granulocyte drug delivery system in various organs

| Organ Time (h) | Heart (μg/g) | Liver (μg/g) | Spleen (μg/g) | Kidney (μg/g) | Lung (μg/g) |
|---|---|---|---|---|---|
| 12 | — | 2.29 | 7.55 | 0.48 | 7.65 |
| 24 | — | 2.34 | 3.63 | 0.41 | 8.87 |
| 48 | — | 2.67 | 2.37 | 0.37 | 5.21 |
| 72 | — | 1.20 | 0.56 | 0.31 | 2.44 |
| 96 | — | 0.42 | 0.37 | 0.29 | 0.71 |
| 120 | — | 1.69 | 0.11 | 0.11 | 0.31 |

It can be known from Tables 7 and 8 that the commercially available levofloxacin injection has the largest distribution in the liver of inflammation model mice, followed by the distribution in the heart, spleen, and kidney, with the distribution in the inflammatory site being less. Compared with the commercially available levofloxacin injection, the neutrophil granulocyte drug delivery system has the largest distribution in the lung and spleen, followed by the distribution in the liver, with the distribution in other organs being less.

5. Targeting Evaluation $AUC_{0-\infty}$, $AUC_{0-120\,h}$ and other parameters in the tissues after the commercially available levofloxacin injection and the neutrophil granulocyte drug delivery system are intravenously injected are calculated by a statistical method in Kinetic 4.0 pharmacokinetic program, and then the relative ratio (Re) and the lung targeting efficiency (Te) are calculated.

The relative ratio (Re) refers to the ratio of AUCs of the neutrophil granulocyte drug delivery system and the commercially available levofloxacin preparation in the lung. A larger Re indicates that the preparation is more potent in targeting the inflammatory tissue than the commercially available preparation. The lung targeting efficiency (Te) refers to the ratio of AUCs of the same preparation in the lung and in other tissues. Where Te is greater than 1, it is indicated that the selectivity of the preparation for the lung is larger than that for other comparative tissues. The larger the Te is, the higher the selectivity of the preparation for the lung tissue infected with bacteria will be, as compared with the selectivity for other comparative tissues.

Figure 9:
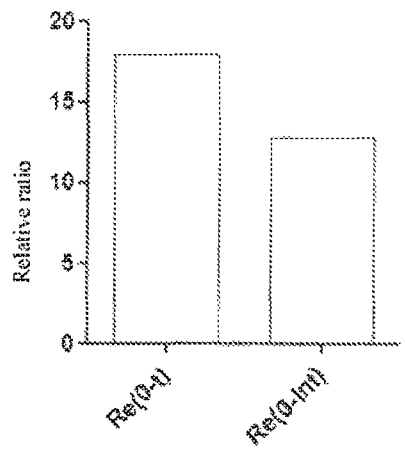
FIG. 9 shows a relative ratio (Re) of a neutrophil granulocyte drug delivery system relative to a commercially available preparation in the inflammatory site of streptococcal pneumonia model mice after administration.
Figure 10:
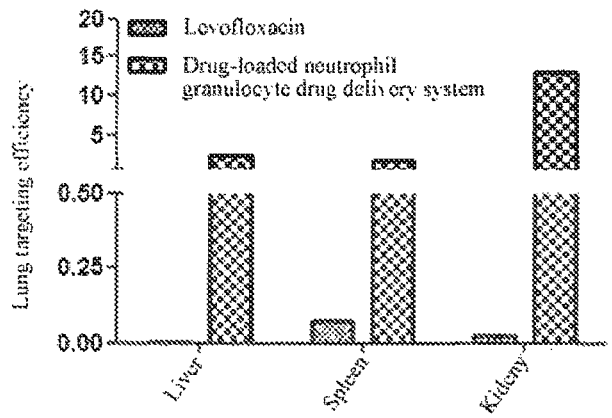
FIG. 10 shows lung targeting efficiencies (Te) of a commercially available preparation and a neutrophil granulocyte drug delivery system in mice after administration.

The $Re_{(0-t)}$ and $Re_{(0-Int)}$ in the inflammatory site of the neutrophil granulocyte drug delivery system relative to the commercially available levofloxacin preparation are shown in FIG. 9, and the Te is greater than 1 in each case (FIG. 10), suggesting that the neutrophil granulocyte drug delivery system is excellent in targeting the inflammation, and can penetrate the blood vessel in the inflammatory site rapidly, and deliver the drug efficiently to the inflammatory tissue.

Figure 11:
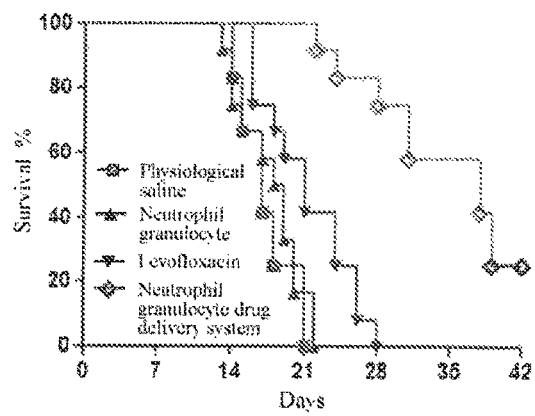
FIG. 11 shows survival time curves of streptococcal pneumonia model mice administered with physiological saline, blank neutrophil granulocytes, a commercially available levofloxacin preparation, and a drug-loaded neutrophil granulocyte drug delivery system.

IV. Pharmacodynamic Evaluation of Neutrophil Granulocyte Drug Delivery System in Streptococcal Pneumonia Model Mouse 48 inflammation model mice were randomized to 4 groups, each group having 12 animals. The 4 groups included a postoperative physiological saline group, a group with simple neutrophil granulocyte, a group with commercially available preparation, and a group with neutrophil granulocyte drug delivery system. The dosage in the group with commercially available preparation was 10 mg/kg; and the animals in the group with neutrophil granulocyte drug delivery system were each intravenously injected with about $5 \times 10^6$ NEs/animal, and the dosage was about 10 mg/kg. All the animals were administered at days 1, 2, 3, 4, 6, 8, and 10 after surgery, and a total of 7 administrations were presented. Groups given with the neutrophil granulocytes of the same density and the physiological saline of the same volume were also set and used as a blank control. The result is shown in FIG. 11. The survival time of the model mice given the commercially available levofloxacin preparation and the physiological saline is similar, and is about 21 days. The survival time of the mice is effectively extended by the neutrophil granulocyte drug delivery system, and some mice are still alive at day 42. This confirms that the neutrophil granulocyte drug delivery system prepared in the present invention can effectively inhibit the occurrence and development of infectious inflammation.

Example 3

Targeting and Pharmacodynamic Evaluation of Ibuprofen-Cationic Liposome-Neutrophil Granulocyte Drug Delivery System in Ear Swelling Model Mice I. Preparation and Characterization of Ibuprofen-Loaded Neutrophil Granulocyte Drug Delivery System The extraction and purification of neutrophil granulocytes were the same as those in Example 1. 5 mg ibuprofen was used to prepare an ibuprofen-cationic liposome, and the preparation process was the same as that in Example 1.

The drug load and encapsulation rate were determined by HPLC, the particle size was measured by a laser particle size analyzer, and the potential was determined. The result is shown in Table 9.

TABLE 9

| Preparation | Potential (mV) | Particle size (nm) | Drug load (%) | Encapsulation rate (%) |
|---|---|---|---|---|
| Ibuprofen-cationic liposome | 37.61 ± 1.12 | 108.5 ± 0.3 | 3.7 | 93 |

Figure 12:
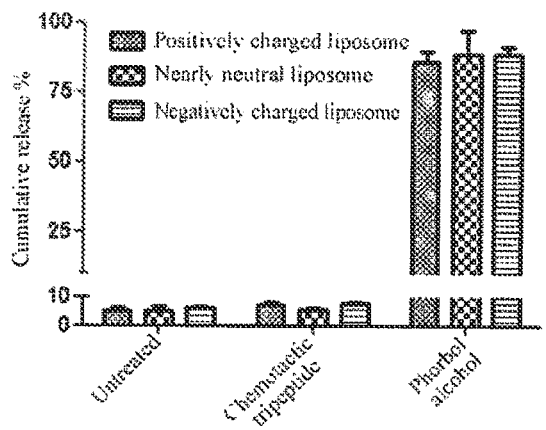
FIG. 12 shows residence of three differently charged ibuprofen-liposomes in neutrophil granulocytes under various physiological conditions simulated in vitro.

The residence of three differently charged ibuprofen-liposomes in neutrophil granulocytes under various physiological conditions simulated in vitro was measured by HPLC. The result is shown in FIG. 12. It can be seen from FIG. 12 that during the normal blood circulation and the process of chemotaxis of inflammatory factors simulated, the cumulative release of the drug from the neutrophil granulocytes drug delivery system is only 7% of the total uptake during the process of chemotaxis, and the release is slow; and in the inflammatory site, the release of the drug is up to 87% of the total uptake when the neutrophil granulocyte are abnormally activated, confirming that the drug can be rapidly and thoroughly released from the cells at the inflammatory site.

II. Establishment of Inflammation Animal Model

Ear swelling mouse model: Round pieces of filter paper that were 7 mm in diameter and soaked with dimethyl benzene were tightly attached for 15 s to the right ears of clean-grade male mice weighed 18-22 g.

III. Targeting Study of Neutrophil Granulocyte Drug Delivery System in Inflammation Model Mice 1. Dosing Regimen 72 mice with inflammation were randomized to 2 groups, each group having 36 animals. Before administration, the mice were fasted, but allowed to free access to water overnight. The 2 groups of mice with inflammation were intravenously injected with the commercially available ibuprofen and the ibuprofen-cationic liposome-neutrophil granulocyte drug delivery system at the tail respectively, where the dosage of ibuprofen was 15 mg/kg in each case. 0.167 h, 0.5 h, 1 h, 2 h, 4 h, 8 h, 12 h, 24 h, 48 h, 72 h, 96 h, and 120 h after administration, the eyeballs were removed to collect the blood, and then the mice were sacrificed. The heart, liver, spleen, kidney, and ear tissues were removed, washed with physiological saline, and weighed after the residual physiological saline was aspirated off with filter paper. The tissues were treated as follows, and the ibuprofen concentration contained in the tissue samples at each time point was determined by HPLC.

2. Sample Treatment

The tissue samples (heart, liver, spleen, kidney, and ear) from the mice with inflammation were weighed, placed in a blood collection tube, added with 2 mL physiological saline, and dispersed by a tissue homogenizer at a high speed, to give a tissue homogenate. 200 µL acetonitrile was added to 200 µL of each tissue homogenate, vortexed for 5 min, and centrifuged for 10 min at 10000×g. The supernatant was analyzed by HPLC and the content of ibuprofen in the tissue samples was calculated according to a linear equation.

3. HPLC Method

Chromatographic column: Inertsil®ODS-SP column (250 mm×4.6 mm×5 µm, GL Sciences Inc., Japan)

Mobile phase: methanol:water-80:20(v:v), with 0.01 mol/L monopotassium phosphate (pH 3.0):acetonitrile=45:55 (v:v)

Detection wavelength: 263 nm

Column temperature: room temperature

Flow rate: 1.0 mL/min

Volume of injection: 20 µL

The tissue homogenate does not interfere with the separation and determination of ibuprofen, and the retention time of ibuprofen is about 10.2 min.

4. In-Vivo Distribution in Mice

TABLE 10

Distribution of ibuprofen in various organs

| Organ Time (h) | Heart (µg/g) | Liver (µg/g) | Spleen (µg/g) | Kidney (µg/g) | Ear (µg/g) |
|---|---|---|---|---|---|
| 0.5 | 6.17 | 12.96 | 5.93 | 2.23 | 0.29 |
| 1 | 3.99 | 10.25 | 3.66 | 3.74 | 0.17 |
| 2 | 2.78 | 7.90 | 1.65 | 2.51 | — |
| 4 | 1.55 | 7.01 | 1.31 | 1.72 | — |
| 8 | 0.43 | 6.32 | 0.68 | 0.57 | — |
| 12 | 0.28 | 3.70 | 0.43 | 0.33 | — |

TABLE 11

Distribution of ibuprofen-cationic liposome-neutrophil granulocyte drug delivery system in various organs

| Organ Time (h) | Heart (µg/g) | Liver (µg/g) | Spleen (µg/g) | Kidney (µg/g) | Ear (µg/g) |
|---|---|---|---|---|---|
| 12 | — | 3.31 | 3.09 | 0.79 | 4.01 |
| 24 | — | 2.90 | 3.22 | 0.63 | 3.22 |
| 48 | — | 2.77 | 2.17 | 0.58 | 2.90 |
| 72 | — | 1.80 | 1.47 | 0.49 | 1.61 |
| 96 | — | 0.63 | 0.61 | 0.33 | 0.70 |
| 120 | — | 0.31 | 0.29 | 0.21 | 0.49 |

It can be known from the above tables that the commercially available ibuprofen injection has the largest distribution in the liver of inflammation model mice, followed by the distribution in the heart, lung, spleen, and kidney, with the distribution in the inflammatory site being less. Compared with the commercially available ibuprofen injection, the neutrophil granulocyte drug delivery system has the largest distribution in the inflammatory site, that is, the ear and the spleen, followed by the distribution in the liver and lung, with the distribution in other organs being less.

5. Targeting Evaluation $AUC_{0-\infty}$, $AUC_{0-120\ h}$ and other parameters in the tissues after the ibuprofen and the neutrophil granulocyte drug delivery system are intravenously injected are calculated by a statistical method in Kinetic 4.0 pharmacokinetic program, and then the relative ratio (Re) and the ear targeting efficiency (Te) are calculated.

The relative ratio (Re) refers to the ratio of AUCs of the neutrophil granulocyte drug delivery system and the commercially available ibuprofen preparation in the ear. A larger Re indicates that the preparation is more potent in targeting the inflammatory tissue (ear) than ibuprofen. The ear targeting efficiency (Te) refers to the ratio of AUCs of the same preparation in the ear and in other tissues. Where Te is greater than 1, it is indicated that the selectivity of the preparation for the ear is larger than that for other comparative tissues. The larger the Te is, the higher the selectivity of the preparation for the non-specific inflammatory site (ear) will be, as compared with the selectivity for other comparative tissues.

Figure 13:
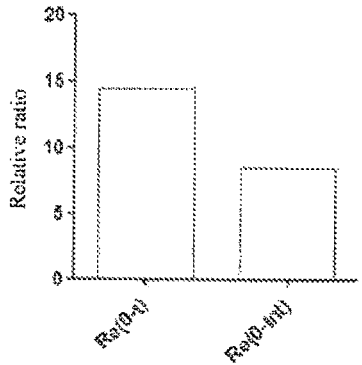
FIG. 13 shows a relative ratio (Re) of a neutrophil granulocyte drug delivery system relative to a commercially available preparation in the inflammatory site of ear swelling model mice after administration.
Figure 14:
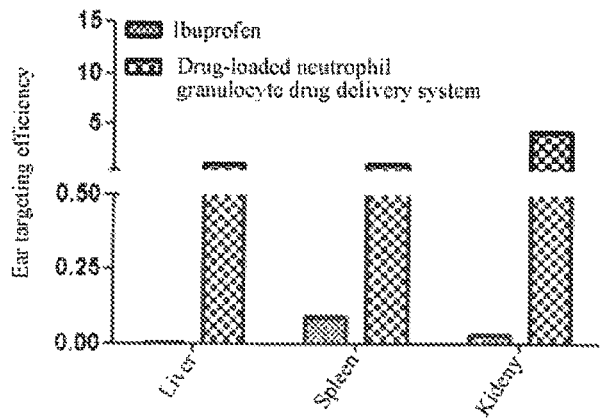
FIG. 14 shows ear targeting efficiencies (Te) of a commercially available preparation and a neutrophil granulocyte drug delivery system in mice after administration.

The $Re_{(0-t)}$ and $Re_{(0-Int)}$ in the inflammatory site of the neutrophil granulocyte drug delivery system relative to the commercially available ibuprofen preparation are shown in FIG. 13, and the Te is greater than 1 in each case (FIG. 14), suggesting that the neutrophil granulocyte drug delivery system is excellent in targeting the inflammation, and can penetrate the blood vessel in the inflammatory site rapidly, and deliver the drug efficiently to the inflammatory tissue.

Figure 15:
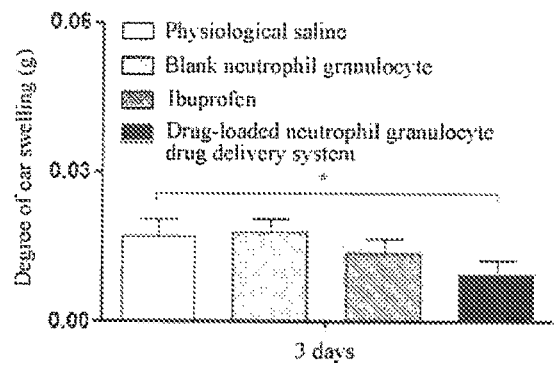
FIG. 15 shows the extent of ear swelling in ear swelling model mice administered with physiological saline, blank neutrophil granulocytes, a commercially available ibuprofen preparation, and a drug-loaded neutrophil granulocyte drug delivery system.

IV. Pharmacodynamic Evaluation of Neutrophil Granulocyte Drug Delivery System in Ear Swelling Model Mice 48 inflammation model mice were randomized to 4 groups, each group having 12 animals. The 4 groups included a postoperative physiological saline group, a group with simple neutrophil granulocyte, a group with commercially available preparation, and a group with neutrophil granulocyte drug delivery system. A control group having 12 mice with primary tumor was also set. The dosage in the group with commercially available preparation was 15 mg/kg; and the animals in the group with neutrophil granulocyte drug delivery system were each intravenously injected with about $5 \times 10^6$ NEs/animal, and the dosage was about 15 mg/kg. All the animals were administered at days 1, 2, 3, 4, 6, 8, and 10 after surgery, and a total of 7 administrations were presented. Groups given with the neutrophil granulocytes of the same density and the physiological saline of the same volume were also set and used as a blank control. Groups given with the neutrophil granulocytes of the same density and the physiological saline of the same volume were also set and used as a blank control. The mice were administrated for 3 consecutive days, and then sacrificed by cervical vertebra dislocation after the 3 administrations. Round specimens were punched from the same portion of the left and the right ears by a 7 mm punch and weighed on an analytical balance. The degree of ear swelling was indicated by the difference in the weight of the ears, and the anti-inflammatory effects of the drugs were compared, as shown in FIG. 15. Compared with the physiological saline group, administration of the commercially available ibuprofen preparation and simple neutrophil granulocytes has no obvious improvement on the degree of ear swelling. In contrast, the degree of ear swelling in the group with neutrophil granulocyte drug delivery system is improved significantly (t test, $p<0.05$). This confirms that the neutrophil granulocyte drug delivery system prepared in the present invention can effectively inhibit the occurrence and development of non-specific inflammation.

Example 4

Targeting and Pharmacodynamic Evaluation of Ibuprofen-Cationic Liposome-Neutrophil Granulocyte Drug Delivery System in Adjuvant Arthritis Model Mice I. Preparation and Characterization of Ibuprofen-Loaded Neutrophil Granulocyte Drug Delivery System The extraction and purification of neutrophil granulocytes were the same as those in Example 1. 10 mg ibuprofen was used to prepare an ibuprofen-cationic liposome, and the preparation process was the same as that in Example 1.

The drug load and encapsulation rate were determined by HPLC, the particle size was measured by a laser particle size analyzer, and the potential was determined. The result is shown in Table 12.

TABLE 12

| Preparation | Potential (mV) | Particle size (nm) | Drug load (%) | Encapsulation rate (%) |
|---|---|---|---|---|
| Ibuprofen-cationic liposome | 37.61 ± 1.12 | 108.5 ± 0.3 | 3.7 | 93 |

Figure 16:
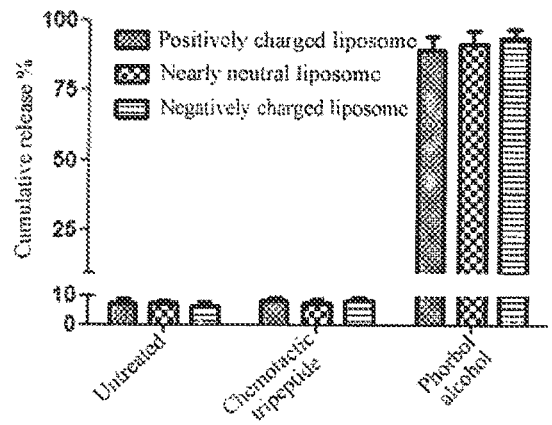
FIG. 16 shows residence of three differently charged ibuprofen-liposomes in neutrophil granulocytes under various physiological conditions simulated in vitro.

The residence of three differently charged ibuprofen-liposomes in neutrophil granulocytes under various physiological conditions simulated in vitro was measured by HPLC. The result is shown in FIG. 16. It can be seen from FIG. 16 that during the normal blood circulation and the process of chemotaxis of inflammatory factors simulated, the cumulative release of the drug is only 8% of the total uptake; and in the inflammatory site, the cumulative release of the drug is up to 91% of the total uptake when the neutrophil granulocyte are abnormally activated, confirming that the drug can be rapidly and thoroughly released from the cells at the inflammatory site.

II. Establishment of Inflammation Animal Model

Adjuvant arthritis mouse model: The BCG vaccine was inactivated for 1 hr in a water bath at 80° C., and ground and mixed fully with autoclaved paraffin, to prepare a 10 mg/ml complete Freund adjuvant (CFA). 0.1 ml CFA was intracutaneously injected into the metatarsal in the right rear foot of the mice for inflammation induction.

III. Targeting Study of Neutrophil Granulocyte Drug Delivery System in Inflammation Model Mice 1. Dosing Regimen 72 mice with inflammation were randomized to 2 groups, each group having 36 animals. Before administration, the mice were fasted, but allowed to free access to water overnight. The 2 groups of mice with inflammation were intravenously injected with the commercially available ibuprofen and the ibuprofen-cationic liposome-neutrophil granulocyte drug delivery system at the tail respectively, where the dosage of ibuprofen was 15 mg/kg in each case. 0.167 h, 0.5 h, 1 h, 2 h, 4 h, 8 h, 12 h, 24 h, 48 h, 72 h, 96 h, and 120 h after administration, the eyeballs were removed to collect the blood, and then the mice were sacrificed. The heart, liver, spleen, kidney, and the metatarsal tissue in the right rear foot were removed, washed with physiological saline, and weighed after the residual physiological saline was aspirated off with filter paper. The tissues were treated as follows, and the ibuprofen concentration contained in the tissue samples at each time point was determined by HPLC.

2. Sample Treatment

The tissue samples (heart, liver, spleen, kidney, and metatarsal in the right rear foot) from the mice with inflammation were weighed, placed in a blood collection tube, added with 2 mL physiological saline, and dispersed by a tissue homogenizer at a high speed, to give a tissue homogenate. 200 μL acetonitrile was added to 200 μL of each tissue homogenate, vortexed for 5 min, and centrifuged for 10 min at 10000×g. The supernatant was analyzed by HPLC and the content of ibuprofen in the tissue samples was calculated according to a linear equation.

3. HPLC Method

Chromatographic column: Inertsil®ODS-SP column (250 mm×4.6 mm×5 μm, GL Sciences Inc., Japan)

Mobile phase: methanol:water=80:20 (v:v), with 0.01 mol/L, monopotassium phosphate (pH 3.0):acetonitrile=45:55 (v:v)

Detection wavelength: 263 nm

Column temperature: room temperature

Flow rate: 1.0 mL/min

Volume of injection: 20 μL

The tissue homogenate does not interfere with the separation and determination of ibuprofen, and the retention time of ibuprofen is about 10.2 min.

4. In-Vivo Distribution in Mice

TABLE 13

Distribution of ibuprofen in various organs

| Organ Time (h) | Heart (μg/g) | Liver (μg/g) | Spleen (μg/g) | Kidney (μg/g) | paw (μg/g) |
|---|---|---|---|---|---|
| 0.5 | 6.35 | 11.87 | 6.01 | 2.79 | 0.43 |
| 1 | 4.24 | 10.02 | 3.99 | 3.90 | 0.37 |
| 2 | 2.99 | 8.32 | 2.42 | 2.68 | 0.21 |
| 4 | 1.87 | 7.37 | 1.98 | 1.91 | — |
| 8 | 0.55 | 6.33 | 1.21 | 0.62 | — |
| 12 | 0.34 | 2.00 | 0.67 | 0.45 | — |

TABLE 14

Distribution of ibuprofen-cationic liposome-neutrophil granulocyte drug delivery system in various organs

| Organ Time (h) | Heart (μg/g) | Liver (μg/g) | Spleen (μg/g) | Kidney (μg/g) | paw (μg/g) |
|---|---|---|---|---|---|
| 12 | — | 3.12 | 3.10 | 0.68 | 5.90 |
| 24 | — | 2.55 | 2.91 | 0.71 | 4.81 |
| 48 | — | 2.51 | 1.95 | 0.88 | 3.22 |
| 72 | — | 1.35 | 1.47 | 0.73 | 2.01 |
| 96 | — | 0.38 | 0.61 | 0.61 | 0.97 |
| 120 | — | 0.12 | 0.29 | 0.34 | 0.60 |

It can be known from the above tables that the commercially available ibuprofen injection has the largest distribution in the liver of inflammation model mice, followed by the distribution in the heart, spleen, and kidney, with the distribution in the inflammatory site being less. Compared with the commercially available ibuprofen injection, the neutrophil granulocyte drug delivery system has the largest distribution in the inflammatory site, that is, the paw, and the spleen, followed by the distribution in the liver, with the distribution in other organs being less.

5. Targeting Evaluation $AUC_{0-\infty}$, $AUC_{0-120\ h}$ and other parameters in the tissues after the ibuprofen and the neutrophil granulocyte drug delivery system are intravenously injected are calculated by a statistical method in Kinetic 4.0 pharmacokinetic program, and then the relative ratio (Re) and the paw targeting efficiency (Te) are calculated.

The relative ratio (Re) refers to the ratio of AUCs of the neutrophil granulocyte drug delivery system and the commercially available ibuprofen preparation in the paw. A larger Re indicates that the preparation is more potent in targeting the inflammatory tissue than ibuprofen. The paw targeting efficiency (Te) refers to the ratio of AUCs of the same preparation in the inflammatory site, that is, the paw, and in other tissues. Where Te is greater than 1, it is indicated that the selectivity of the preparation for the inflammatory site (the metatarsal in the right rear foot) is larger than that for other comparative tissues. The larger the Te is, the higher the selectivity of the preparation for the non-specific inflammatory site (the metatarsal in the right rear foot) will be, as compared with the selectivity for other comparative tissues.

Figure 17:
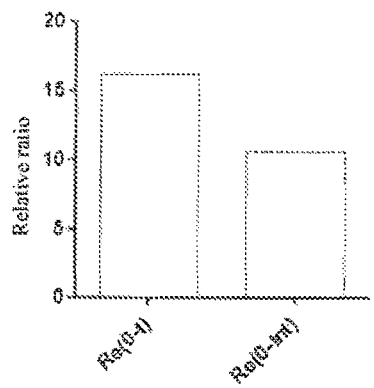
FIG. 17 shows a relative ratio (Re) of a neutrophil granulocyte drug delivery system relative to a commercially available preparation in the inflammatory site of adjuvant arthritis model mice after administration.
Figure 18:
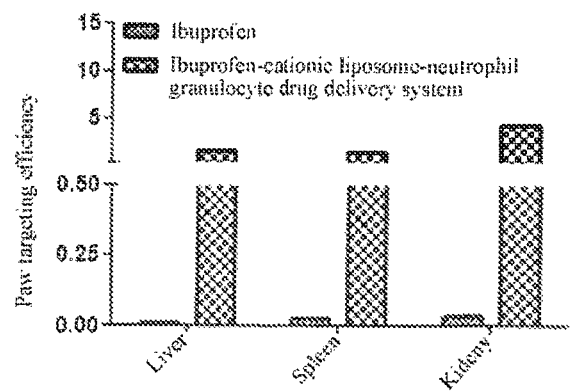
FIG. 18 shows paw targeting efficiencies (Te) of a commercially available preparation and a neutrophil granulocyte drug delivery system in mice after administration.

The $Re_{0-t}$ and $Re_{(0-Int)}$ in the inflammatory site of the neutrophil granulocyte drug delivery system relative to the commercially available ibuprofen preparation are shown in FIG. 17, and the Te is greater than 1 in each case (FIG. 18), suggesting that the neutrophil granulocyte drug delivery system is excellent in targeting the inflammation, and can penetrate the blood vessel in the inflammatory site rapidly, and deliver the drug efficiently to the inflammatory tissue.

IV. Pharmacodynamic Evaluation of Neutrophil Granulocyte Drug Delivery System in Adjuvant Arthritis Model Mice 48 inflammation model mice were randomized to 4 groups, each group having 12 animals. The 4 groups included a physiological saline group, a group with simple neutrophil granulocyte, a group with commercially available preparation, and a group with neutrophil granulocyte drug delivery system after the inflammation model was established. The dosage in the group with commercially available preparation was 15 mg/kg, and the animals in the group with neutrophil granulocyte drug delivery system were each intravenously injected with about $5 \times 10^6$ NEs/animal, and the dosage was about 15 mg/kg. All the animals were administered at days 1, 2, 3, 4, 6, 8, and 10 after surgery, and a total of 7 administrations were presented. Groups given with the neutrophil granulocytes of the same density and the physiological saline of the same volume were also set and used as a blank control. After administration, the osteoarthritis index was scored every 3 days, to observe the secondary lesions in each group of mice.

Figure 19:
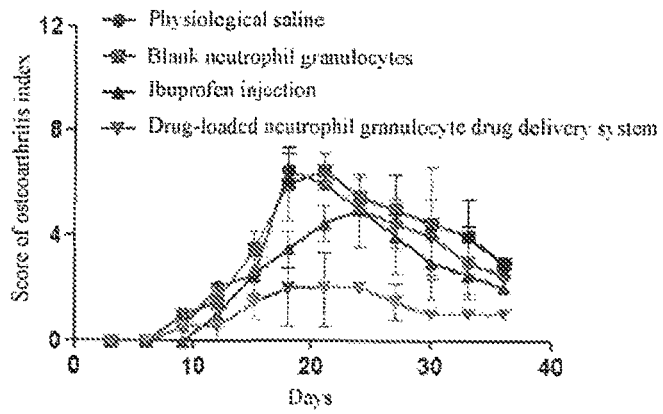
FIG. 19 shows scores of osteoarthritis index of adjuvant arthritis model mice administered with physiological saline, blank neutrophil granulocytes, a commercially available ibuprofen preparation, and a drug-loaded neutrophil granulocyte drug delivery system.

Scoring criteria of osteoarthritis index for the paw: 0=normal; 1=erythema and mild swelling of the ankle joint; 2=erythema and slight swelling of the ankle joint to the metatarsal joint or metacarpal joint; 3=erythema and moderate swelling of the ankle to metatarsophalangeal joint or palmar joint; 4=erythema and severe swelling of the ankle to the phalangeal joint. Each mouse was scored 12 at most. The result is shown in FIG. 19. In terms of the peak score of the osteoarthritis index and the time at which the peak score occurs, compared with the physiological saline group, there is no significant difference between the group administered simply with neutrophil granulocytes and the physiological saline group. After the commercially available ibuprofen preparation is dosed, the peak score is reduced and the time at which the peak score occurs is prolonged somewhat. However, after the neutrophil granulocyte drug delivery system is dosed, the peak score is reduced and the time at which the peak score occurs is prolonged considerably. This confirms that the neutrophil granulocyte drug delivery systems prepared in the present invention can effectively inhibit the occurrence and development of allergic inflammation.

What is claimed is:

1. A drug delivery system comprising:
   purified cells including neutrophil granulocytes; and
   a synthetic drug loaded into the neutrophil granulocytes or onto the surface of the neutrophil granulocytes, wherein:
   more than 90% of the purified cells are the neutrophil granulocytes; and
   the drug is initially loaded into a nonmagnetic nanocarrier to prepare a nonmagnetic nanopreparation and then the nonmagnetic nanopreparation is loaded into the neutrophil granulocytes or onto the surface of the neutrophil granulocytes.

2. The drug delivery system according to claim 1, wherein the nonmagnetic nanocarrier is a positively charged, a negatively charged, or a nearly neutral nanocarrier having a particle size of 1-1000 nm.

3. The drug delivery system according to claim 1, wherein the nonmagnetic nanocarrier includes at least one member selected from the group consisting of gold nanoparticles/nanorods, mesoporous silica nanoparticles, graphene, liposomes, micelles, nanoemulsions, nanospheres, nanocapsules, microspheres, pellets, and dendritic polymers.

4. The drug delivery system according to claim 1, wherein the drug is one or more selected from the group consisting of efferent nervous system drugs, central nervous system drugs, cardiovascular system drugs, respiratory and digestive system drugs, antibacterial or antiviral drugs, and antineoplastic agents.

5. The drug delivery system according to claim 1, wherein the drug is one or more selected from diazepam, phenytoin sodium, chlorpromazine, fluoxetine, methadone, meclofenoxate, bethanechol chloride, atropine sulfate, isoprenaline, chlorpheniramine maleate, procaine hydrochloride, propranolol hydrochloride, verapamil hydrochloride, amiodarone hydrochloride, losartan, nitroglycerin, dobutamine, simvastatin, clopidogrel, prazosin, cimetidine, difenidol, cisaprid, bifendate, aspirin, indomethacin, mechlorethamine hydrochloride, fluorouracil, paclitaxel, amoxicillin, tetracycline, aminoglycoside, roxithromycin, chloramphenicol, levofloxacin, isoniazid, sulfadiazine, fluconazole, amantadine hydrochloride, fluoroquinol phosphate, glibenclamide, or hydrochlorothiazide.

6. A method for drug delivery, comprising injecting the drug delivery system according to claim 1 into a human to deliver the drug to an inflammation site of the human.

7. The method according to claim 6, wherein the inflammation site results from an infectious inflammation, non-specific inflammation, allergic inflammation, or inflammation caused by an inflammation-related disease.

8. The method according to claim 7, wherein the infectious inflammation is caused by viruses, bacteria or bacterial products; the non-specific inflammation is redness or pain caused by surgery or trauma; the allergic inflammation is lupus dermatitis, allergies asthma, or rheumatoid arthritis; and the inflammation-related disease is a relapsed tumor after surgery, atherosclerosis, or hypoxic ischemic encephalopathy.

9. The drug delivery system according to claim 1, wherein the drug has therapeutic efficacy against inflammation and/or an inflammation-related disease.

10. The drug delivery system according to claim 1, wherein the nonmagnetic nanocarrier and nonmagnetic nanopreparation are positively charged.

11. A delivery system for a therapeutic or detectable substance, comprising:
purified cells including neutrophil granulocytes;
a nonmagnetic nanocarrier in the neutrophil granulocytes or on the surface of the neutrophil granulocytes; and
the therapeutic or detectable substance loaded into the nonmagnetic nanocarrier, wherein:
more than 90% of the purified cells are the neutrophil granulocytes;
the therapeutic or detectable substance is initially loaded into the nonmagnetic nanocarrier to prepare a nonmagnetic nanopreparation and then the nonmagnetic nanopreparation is loaded into the neutrophil granulocytes or onto the surface of the neutrophil granulocytes; and
the nonmagnetic nanocarrier includes at least one member selected from the group consisting of gold nanoparticles/nanorods, mesoporous silica nanoparticles, graphenes, liposomes, micelles, nanoemulsions, nanospheres, nanocapsules, microspheres, pellets, and dendritic polymers.

12. The delivery system according to claim 11, wherein the therapeutic or detectable substance is a therapeutic substance that is a drug, DNA, RNA, protein, or polypeptide.

13. The delivery system according to claim 11, wherein the therapeutic or detectable substance is a therapeutic substance that is a synthetic drug.

14. The delivery system according to claim 11, wherein the therapeutic or detectable substance is a detectable substance that is a probe or developing agent.

15. A diagnostic method comprising injecting the delivery system according to claim 11 into a human to deliver a detectable substance to an inflammation site of the human.

16. The delivery system according to claim 11, wherein the therapeutic or detectable substance is a detectable substance.

17. The delivery system according to claim 11, wherein the nonmagnetic nanocarrier and nonmagnetic nanopreparation are positively charged.

* * * * *